US008822379B2

(12) United States Patent
Goodwin

(10) Patent No.: US 8,822,379 B2
(45) Date of Patent: *Sep. 2, 2014

(54) PLANT NUTRIENT CONCENTRATE COMPOSITION

(75) Inventor: Brian B. Goodwin, Collierville, TN (US)

(73) Assignee: FBSciences Holdings, Inc., Collierville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/602,982

(22) Filed: Sep. 4, 2012

(65) Prior Publication Data

US 2013/0005570 A1 Jan. 3, 2013

Related U.S. Application Data

(62) Division of application No. 12/875,447, filed on Sep. 3, 2010, now Pat. No. 8,466,087.

(60) Provisional application No. 61/239,774, filed on Sep. 3, 2009.

(51) Int. Cl.
| | |
|---|---|
| A01N 55/00 | (2006.01) |
| A01N 57/00 | (2006.01) |
| A01N 59/00 | (2006.01) |
| A01N 63/02 | (2006.01) |
| A01N 65/00 | (2009.01) |
| C05B 17/00 | (2006.01) |
| C05F 11/00 | (2006.01) |

(52) U.S. Cl.
USPC ........... 504/113; 504/102; 504/118; 504/122; 504/123; 504/189; 504/193; 504/194; 71/11; 71/23; 71/15; 71/16; 71/17; 71/18; 71/19; 71/20; 71/21; 71/31; 71/63

(58) Field of Classification Search
CPC ....... A01N 25/02; A01N 27/00; A01N 62/02; A01N 65/00; C05F 11/02; C05G 3/0076
USPC ......... 504/113, 102, 118, 122, 123, 189, 193, 504/194; 71/23, 24, 11, 15, 16, 17, 18, 19, 71/20, 21, 22, 31, 63
See application file for complete search history.

(56) References Cited

U.S. PATENT DOCUMENTS

| | | | |
|---|---|---|---|
| 2,200,532 A | 12/1939 | Sherman | |
| 3,958,016 A | 5/1976 | Galle et al. | |
| 4,069,034 A | 1/1978 | Hoover | |
| 4,245,432 A | 1/1981 | Dannelly | |
| 4,249,343 A | 2/1981 | Dannelly | |
| 4,272,920 A | 6/1981 | Dawson | |
| 4,337,077 A | 6/1982 | Rutherford | |
| 4,367,609 A | 1/1983 | Lloyd | |
| 462,469 A | 11/1986 | Humbert | |
| 4,698,090 A | 10/1987 | Marihart | |
| 4,769,221 A | 9/1988 | Marihart | |
| 4,786,307 A | 11/1988 | Marihart | |
| 4,828,600 A | 5/1989 | McCabe et al. | |
| 4,875,921 A | 10/1989 | Paau | |
| 4,878,936 A | 11/1989 | Handelsman et al. | |
| 4,952,229 A * | 8/1990 | Muir | 71/7 |
| 5,026,416 A | 6/1991 | Alexander | |
| 5,044,116 A | 9/1991 | Gago et al. | |
| 5,087,475 A | 2/1992 | Bazin et al. | |
| 5,129,180 A | 7/1992 | Stewart | |
| 5,178,661 A | 1/1993 | Van Der Watt et al. | |
| 518,347 A | 2/1993 | Masuda | |
| 5,204,368 A | 4/1993 | Cronje et al. | |
| 5,250,500 A | 10/1993 | Jones et al. | |
| 5,300,127 A | 4/1994 | Williams | |
| RE34,670 E | 7/1994 | Williams et al. | |
| 5,525,131 A | 6/1996 | Asano | |
| 559,394 A | 1/1997 | Kinnersley | |
| 5,599,769 A | 2/1997 | Hacker et al. | |
| 5,665,671 A | 9/1997 | Zanin | |
| 5,747,020 A | 5/1998 | Rutherford et al. | |
| 5,849,320 A | 12/1998 | Turnblad et al. | |

(Continued)

FOREIGN PATENT DOCUMENTS

| | | |
|---|---|---|
| CA | 1328238 | 4/1994 |
| CA | 2056107 | 7/1998 |

(Continued)

OTHER PUBLICATIONS

Dixon et al., "Flavonoids adn isoflavonoids—a gold mine for metabolic engineering," 1999, Trends in Plant Science, 4(10): 394-400.*
Kafe-F, Kafe-F Improves Fertilizer Efficiency and Nutrient Uptake, copyright 2009-2013 [retrieved on Mar. 7, 2013] Retrieved from the Internet: <URL: http://www.fbsciences.com/kafe-f/.*
Dixon et al., "Flavonoids and isoflavonoids—a gold mine for metabolic engineering," 1999, Trends in Plant Science, 4(10): 394-400.*
Carbon Boost-S and Kafe-F. Datasheet [online]. FBSciences, copyright 2009-2013 [retrieved on Mar. 7, 2013] Retrieved from the Internet: <URL: http://www.fbsciences.com/crop-nutrition?/.*
Carbon Boost-S. Label [online]. FBSciences, undated material [retrieved on Mar. 7, 2013] Retrieved from the Internet: <URL: http://www.waverlycoop.com/images/EO103301/Carbon_Boost_S.pdf.*

(Continued)

Primary Examiner — Jane C Oswecki
(74) Attorney, Agent, or Firm — Christopher J. Knors; Moore & Van Allen PLLC

(57) ABSTRACT

A seed composition comprising a seed and a first component comprising an agriculturally acceptable complex mixture of dissolved organic material characterized by natural organic matter that is partially humified and methods of seed treating. A method comprising contacting a seed with a first component comprising an agriculturally acceptable complex mixture of dissolved organic material characterized by natural organic matter that is partially humified, where the first component enhances at least one of germination, emergence, root development, seedling vigor, seedling growth, mortality resistance, chlorophyll production, cold resistance, water log resistance, and nutrient uptake compared to similar seed not contacted with the first component.

3 Claims, No Drawings

(56) References Cited

U.S. PATENT DOCUMENTS

| | | | |
|---|---|---|---|
| 5,928,997 A | 7/1999 | Bauer et al. | |
| 5,951,978 A | 9/1999 | Red'kina | |
| 6,022,744 A | 2/2000 | Tetteroo et al. | |
| 607,498 A | 6/2000 | King | |
| 6,077,505 A | 6/2000 | Parke et al. | |
| 6,080,220 A | 6/2000 | Sequi et al. | |
| 6,080,319 A | 6/2000 | Alther | |
| 6,083,877 A | 7/2000 | Kinnersley et al. | |
| 6,090,750 A | 7/2000 | Chollet et al. | |
| 6,121,193 A | 9/2000 | Segaud et al. | |
| 6,199,318 B1 | 3/2001 | Stewart et al. | |
| 6,261,996 B1 | 7/2001 | Klittich et al. | |
| 6,277,787 B1 | 8/2001 | Malefyt et al. | |
| 628,470 A1 | 9/2001 | Jong | |
| 6,372,008 B1 | 4/2002 | Boote et al. | |
| 6,434,884 B1 | 8/2002 | Hartung | |
| 644,781 A1 | 9/2002 | Choi | |
| 6,453,608 B1 | 9/2002 | Flanagan et al. | |
| 6,458,747 B1 | 10/2002 | Kulik | |
| 6,557,298 B2 | 5/2003 | Obert et al. | |
| 666,984 A1 | 12/2003 | Nguyen | |
| 667,337 A1 | 1/2004 | Choi | |
| 6,698,137 B2 | 3/2004 | Muhr | |
| 6,855,536 B2 | 2/2005 | Loh et al. | |
| 688,444 A1 | 4/2005 | Choi | |
| 689,990 A1 | 5/2005 | Choi | |
| 6,911,415 B1 * | 6/2005 | Ueland et al. | 504/119 |
| 691,665 A1 | 7/2005 | Arndt | |
| 7,001,869 B2 | 2/2006 | Johnson | |
| 7,003,914 B2 | 2/2006 | Legro et al. | |
| 7,182,951 B1 | 2/2007 | Balachander et al. | |
| 7,213,367 B2 | 5/2007 | Wertz et al. | |
| 729,127 A1 | 11/2007 | Bourke | |
| 7,393,678 B2 | 7/2008 | Triplett et al. | |
| 7,510,590 B2 | 3/2009 | Anaya-Olvera | |
| 754,096 A1 | 6/2009 | Sengupta | |
| 7,687,434 B2 | 3/2010 | De Billot et al. | |
| 776,366 A1 | 7/2010 | Vero | |
| 778,547 A1 | 8/2010 | Vero | |
| 8,466,087 B2 * | 6/2013 | Goodwin | 504/100 |
| 8,614,165 B2 * | 12/2013 | Goodwin | 504/100 |
| 2002/0053229 A1 | 5/2002 | Varshovi | |
| 2002/0095864 A1 | 7/2002 | Obert et al. | |
| 2002/0134012 A1 | 9/2002 | Ding et al. | |
| 2003/0044382 A1 | 3/2003 | Selvig et al. | |
| 2003/0130120 A1 | 7/2003 | Ziemer et al. | |
| 2003/0185900 A1 | 10/2003 | Choi et al. | |
| 2003/0206967 A1 | 11/2003 | Choi et al. | |
| 2003/0228679 A1 | 12/2003 | Smith et al. | |
| 2003/0228981 A1 | 12/2003 | Wertz et al. | |
| 2004/0063582 A1 | 4/2004 | Johnson | |
| 2004/0077498 A1 | 4/2004 | Lynch | |
| 2004/0118040 A1 | 6/2004 | Asrar et al. | |
| 2004/0261481 A1 | 12/2004 | Anaya-Olvera | |
| 2005/0065034 A1 | 3/2005 | Miele et al. | |
| 2005/0197251 A1 | 9/2005 | Ding et al. | |
| 2005/0197253 A1 | 9/2005 | Stoller et al. | |
| 2005/0220834 A1 | 10/2005 | Wang et al. | |
| 2006/0032120 A1 | 2/2006 | McPherson | |
| 2006/0032281 A1 | 2/2006 | Meyer | |
| 2006/0229203 A1 | 10/2006 | Peltonen et al. | |
| 2007/0039365 A1 | 2/2007 | King et al. | |
| 2007/0068072 A1 | 3/2007 | Xavier et al. | |
| 2007/0074451 A1 | 4/2007 | Pearce et al. | |
| 2007/0095118 A1 | 5/2007 | Evers et al. | |
| 2007/0212772 A1 | 9/2007 | Hill et al. | |
| 2007/0249498 A1 | 10/2007 | Van Der Drift | |
| 2008/0004178 A1 | 1/2008 | Ding et al. | |
| 2008/0242544 A1 | 10/2008 | Duckham et al. | |
| 2008/0274885 A1 | 11/2008 | Martin et al. | |
| 2009/0105076 A1 | 4/2009 | Stewart et al. | |
| 2009/0105077 A1 | 4/2009 | Bhatti et al. | |
| 2009/0199314 A1 | 8/2009 | Gaudillat | |
| 2010/0010089 A1 | 1/2010 | Van Dyke et al. | |
| 2010/0016162 A1 | 1/2010 | Goodwin | |
| 2011/0053771 A1 | 3/2011 | Goodwin | |
| 2011/0077155 A1 | 3/2011 | Goodwin | |
| 2011/0078816 A1 | 3/2011 | Goodwin | |
| 2011/0174031 A1 | 7/2011 | Bargiacchi et al. | |
| 2012/0015805 A1 | 1/2012 | Goodwin | |
| 2012/0196747 A1 | 8/2012 | Goodwin | |
| 2013/0005570 A1 | 1/2013 | Goodwin | |

FOREIGN PATENT DOCUMENTS

| | | |
|---|---|---|
| CN | 1111932 (A) | 11/1995 |
| CN | 1356061 (A) | 7/2002 |
| CN | 1443439 A | 9/2003 |
| EP | 164908 | 9/1989 |
| EP | 560943 | 3/1999 |
| EP | 1216976 | 6/2002 |
| EP | 949975 | 10/2002 |
| EP | 1464635 | 10/2004 |
| EP | 1238714 | 3/2005 |
| EP | 1757187 | 2/2007 |
| EP | 2345628 | 7/2011 |
| JP | H04-258225 A | 9/1992 |
| JP | 05-194951 | 8/1993 |
| JP | 10-273409 | 10/1998 |
| JP | 2000092918 A | 4/2000 |
| JP | 2008-501353 | 1/2008 |
| KR | 10-0835240 | 6/2008 |
| WO | WO9013420 | 11/1990 |
| WO | WO9015138 | 12/1990 |
| WO | WO9210081 | 6/1992 |
| WO | WO9517806 | 7/1995 |
| WO | WO0140441 | 6/2001 |
| WO | WO 2002041903 | 5/2002 |
| WO | WO03020028 | 3/2003 |
| WO | WO03020837 | 3/2003 |
| WO | WO03094614 | 11/2003 |
| WO | WO2007024753 | 3/2007 |
| WO | WO2007143791 | 12/2007 |
| WO | WO2009068195 | 6/2009 |
| WO | WO2009068213 | 6/2009 |

OTHER PUBLICATIONS

Kafe-F, Kafe-F Improves Fertilizer Efficiency and Nutrient Uptake, copyright 2009-2013 [retrieved on Mar 7, 2013] Retrieved from the Internet: <URL: http://www.fbsciences.com/kafe-f/.*

Wershaw, Robert L., Evaluation of Conceptual Models of Natural Organic Matter (Humus) From a Consideration of the Chemical and Biochemical Processes of Humification, Scientific Investigations Report 2004-5121, US Department of the Interior, US Geological Survey (2004).

Pandey, Girdhar, et al., "ABR1, an APETALA2-Domain Transcription Factor that Functions as a Repressor of ABA Response in *Arabidopsis*", Plant Physiology, vol. 139, No. 3, pp. 1185-1193 (Nov. 2005).

http://ihss.gatech.edu/ihss2/whatarehs.html, What are Humic Substances? (Dec. 2007).

http://ihss.gatech.edu/ihss2/sources.html, Source Materials for IHSS Samples (Aug. 1, 2009).

Landec AG Inc.—Seeds of Innovation, IntelliCoat Early Corn, Reference Guide, (1997).

Schulze, et al., Environment as Stress Factor: Stress Physiology of Plants, Plant Ecology, Springer, pp. 7-11 (2005).

Jonak, Claudia, et al., Stress signaling in plants: A mitogen-activated protein kinase pathway is activated by cold and drought, PNAS, vol. 93, 11274-11279 (Oct. 1996).

Zhang, Xunzhong, Influence of Plant Growth Regulators on Turfgrass Growth, Antioxidant Status, and Drought Tolerance, Dissertation. Virginia Polytechnic Institute and State University (Jul. 1997).

Johnson, Kim, et al., Genetic control of plant organ growth, New Phytologist, vol. 191, 319-333 (2001).

Goodwin, Brian B., Non-Final Office Action for U.S. Appl. No. 12/892,564 dated Jan. 16, 2013.

Goodwin, Brian B., Non-Final Office Action for U.S. Appl. No. 12/892,486 dated Aug. 16, 2012.

(56) References Cited

OTHER PUBLICATIONS

Goodwin, Brian B., Notice of Allowance and Fees for U.S. Appl. No. 12/875,447 dated Dec. 26, 2012.
Chinese Patent Office, Chinese Patent Application No. 201080039321.2 Office Action dated May 22, 2013 with English translation, pp. 1-12.
Korean Intellectual Propery Office, PCT International Preliminary Report on Patentability and Written Opinion of the International Searching Authority for International Appication No. PCT/US2010/047770 dated Mar. 6, 2012, pp. 1-6.
Collaberative, "Humus", Wikipedia. Internet Article, Jan. 1, 2002 (retreived on Jun. 24, 2013) Retrieved from the Internet. <URL:http//en.wikipedia.org/wiki/humus/>.
Delta Farm Press "High Yields with Carbon Power Products", Jul. 23, 2009, URL: http://deltafarmpress.com/equipment/agribusiness-high-yeilds-carbon-ower-products, downloaded on Sep. 4, 2013, pp. 1-5.
European Patent Office, Supplementary European Search Report for European Patent Application No. 10814542.6, dated Sep. 13, 2013, pp. 1-9.
Fbsciences, "Npk Enhancement Products Boost Crop Yields", Fbsciences News, Sep. 5, 2008, RUL: http://www.fbsadvantage.com/news/npk-enhancements-productes-boost-crop-yields/?year=2008&month=9, downloaded Aug. 4. 2013, p. 1.
Fluvic Acid Data Sheet. Datasheet [online]. ChemnetBase, 2011 [retrieved on Sep. 22, 2011]. Retrived from the Internet<http://ccd.chemnetbase.com/AAA00.entry?parentCHNumber=BFG52&exno=BFG52>, 3 pages.
Remus-Borel, Wilfred, et al.,"Silicon induces antifungal compounds in powdery mildew-infected wheat", Physiological and Molecular Plant Pathology, vol. 66, pp. 108-115 (2005).
Shandong Chuangxin Humic Acid Technology Co., Ltd., Humic Acid + Amino Acid Powder. <http://www.humicacidcorp.com/>, p. 1, 2009.
Shandong Chuangxin Humic Acid Technology Co., Ltd., Nitro Humic Acid. <http://www.humicacidcorp.com/>, pp. 1-2, 2009.
Steinberg, et al.,"Humic Substances, Part 2: interactions with Organisims". Environ Sci Pollut Res Int, 15 (2), pp. 128-235 (2008).
WPI/Thomson, "XP-002712268", Thomson Scientific, Abstract of JP19980275483 and GB2000-311021, Apr. 4, 2000, p. 1.
Chinese Patent Office, Chinese Patent Application No. 201080039321.2 Office Action dated Mar. 12, 2014, pp. 1-24.

* cited by examiner

PLANT NUTRIENT CONCENTRATE COMPOSITION

CROSS-REFERENCE TO RELATED APPLICATIONS

This is a divisional application of application Ser. No. 12/875,447, filed Sep. 3, 2010, which is incorporated herein by reference in its entirety.

TECHNICAL FIELD

The present invention relates to compositions and seed treatments for improving overall seed and plant health and methods for reducing susceptibility of a seed or plant to stress and/or disease or improving plant production.

BACKGROUND

Various mixtures of organic compounds have been proposed in the art as fertilizer additives. Specifically, a humic acid composition, Bio-Liquid Complex™, is stated by Bio Ag Technologies International (1999) www.phelpstek.com/portfolio/humic_acid.pdf to assist in transferring micronutrients, more specifically cationic nutrients, from soil to plant.

TriFlex™ Bloom Formula nutrient composition of American Agritech is described as containing "phosphoric acid, potassium phosphate, magnesium sulfate, potassium sulfate, potassium silicate[and] sodium silicate." TriFlex™ Grow Formula 2-4-1 nutrient composition of American Agritech is described as containing "potassium nitrate, magnesium nitrate, ammonium nitrate, potassium phosphate, potassium sulfate, magnesium sulfate, potassium silicate, and sodium silicate." Both compositions are said to be "fortified with selected vitamins, botanical tissue culture ingredients, essential amino acids, seaweed, humic acid, fulvic acid and carbohydrates." See www.horticulturesource.com/product_info.php/products_id/82. These products are said to be formulated primarily for "soilless hydrogardening" (i.e., hydroponic cultivation) of fruit and flower crops, but are also said to outperform conventional chemical fertilizers in container soil gardens. Their suitability or otherwise for foliar application as opposed to application to the hydroponic or soil growing medium is not mentioned. See www.americanagritech.com/product/product_detail.asp?ID=I &pro_id_pk=4-0.

The trademark Monarch™, owned by Actagro, LLC is a fertilizer composition containing 2-20-15 primary plant nutrients with 3% non plant food organic compositions derived from natural organic materials.

SUMMARY

There is now provided a seed composition comprising: a seed; and a first component comprising an agriculturally acceptable complex mixture of dissolved organic material characterized by natural organic matter that is partially humified; and optionally, a second component selected from agriculturally acceptable sources of pesticides, fertilizers, growth regulators, and mixtures thereof.

There is still further provided a method of seed treating, the method comprising contacting a seed with a first component comprising an agriculturally acceptable complex mixture of dissolved organic material characterized by natural organic matter that is partially humified.

There is still further provided a method comprising contacting a seed with a first component comprising an agriculturally acceptable complex mixture of dissolved organic material characterized by natural organic matter that is partially humified, where the first component enhances one or more of germination, emergence, root development, chlorophyll production, cold resistance, water log resistance, and nutrient uptake compared to a seed not contacted with the first component. The method can further comprise contacting with the first component a foliar surface of a plant derived from the seed contacted with the first component.

There is still further provided a method for improving growth or nutrition of a plant, comprising applying a composition comprising the first component and a pesticide, optionally a plant nutrient, to a seed, a foliar surface of the plant, or the locus of the plant.

There is still further provided a method for reducing delayed or attenuated growth or yield of a genetically modified (GM) plant having a specific tolerance to a chemical antagonist, the method comprising contacting the foliar surface, locus or seed of a GM plant a composition comprising a first component comprising an agriculturally acceptable mixture of partially humified natural organic matter, a chemical antagonist associated with the genetic modification of the plant; and optionally, a plant nutrient.

There is still further provided a plant nutrient composition comprising, in aqueous solution, a first component comprising an agriculturally acceptable mixture of partially humified natural organic matter; and a second component selected from at least one pesticide, fertilizer, growth regulator, and mixtures thereof.

BRIEF DESCRIPTION OF THE DRAWINGS

None.

DETAILED DESCRIPTION

Disclosed and described herein is, in part, plant growth, nutrient, or health compositions and seed treatments and coatings thereof, comprising a first component comprising a natural organic material of defined composition and optionally, a second component comprising at least one pesticide (individually or collectively, a herbicide, an insecticide, a fungicide, a bactericide, an anti-viral, plant nutrient, or combinations thereof). Compositions disclosed and described herein vary depending on the intended method of application, the plant species to which they are to be applied, growing conditions of the plants, and other factors.

Compositions disclosed and described herein can take the form of aqueous solutions, oil-in-water emulsions, or water-in-oil emulsions. Small amounts of insoluble material can optionally be present, for example in suspension in the medium, but it is generally preferred to minimize the presence of such insoluble material.

The First Component

The first component of the composition disclosed and described herein comprises a mixture of organic molecules isolated and extracted from sources rich in natural organic matter into an aqueous solution. The natural organic matter is primarily derived from plant materials that have been modified to varying degrees over time in a soil environment. Some of the plant materials have been recently deposited in the environment. At least a part of the natural organic matter has passed through a partial process of humification to become partially humified natural organic matter. Humification includes microbial, fungal, and/or environmental (heat, pressure, sunlight, lightning, fire, etc.) degradation and/or oxidation of natural organic matter. Most preferably, the first component contains natural organic matter that has not substantially undergone humification (partially humified natural organic matter). In one aspect, the natural organic matter is obtained from environments typically containing or providing anywhere between about 5 ppm, to about 500 ppm of dissolved organic matter (DOM). In other aspects, the natural organic matter is obtained from environments typically containing or providing between about 500 ppm to about 3000 ppm or more DOM.

Natural organic matter is extremely complex, with thousands of compounds generally present, depending upon the source and the environmental conditions prevalent about the source. Humic substances such as Fulvic Acid (CAS No. 479-66-3) and Humic Acid (CAS No. 1415-93-6) are examples of organic complexes that are derived from natural organic matter, however, The first component is chemically and biologically unique from Fulvic and Humic acid, as detailed below.

The first component contains dissolved organic matter, the organic matter being formed during the process of humification as described above, such as microbial, fungicidal, and/or environmental (heat, pressure, sunlight, lightning, fire, etc.) degradation processes. Other natural or synthetic natural organic matter degradation processes may be involved or may be used. In one aspect, the first component contains predominately natural organic matter that has not undergone substantial humification (e.g., partially humified natural organic matter). The amount of humification may be determined and characterized using known methods, for example, by 13C NMR.

In one aspect, the first component is obtained by removing a natural organic matter from its source, optionally processing, and/or concentrating to provide the first component having a dissolved organic matter (DOM) concentration level of from anywhere between about 10× to about 5000× relative to its original source. In another aspect, the first component concentrations of dissolved organic matter (DOM) concentration level can be between about 7500× up to about 50,000×. The first component may be adjusted such that the concentration of DOM is between about 10 ppm to about 700,000 ppm. Preferably, the first component may be adjusted such that the concentration of DOM is between about 1000 ppm to about 500,000 ppm. The first component may be adjusted to a DOM value represented by any ppm value between 1000 ppm and 50,000 ppm, inclusive of any ppm value in 500 ppm increments (e.g., 10,500 ppm, 11,000 ppm, 11,500 ppm, 12,000 ppm, etc.) in aqueous solution. Other DOM concentrations may be used, for example, an extremely concentrated composition of between about 75,000 ppm and about 750,000 ppm can be prepared. For example, a concentrate of about 30,000× of the original source can contain about 550,000 ppm of DOM. In certain aspects, the first component are approximately between about 91% to about 99% water, the remaining organic material being primarily DOM with minor amounts of alkali-, alkali earth-, and transition metal salts. In yet other aspects, the DOM of the first component has been dried or lyophilized in a form suitable for reconstitution with an aqueous solution.

The first component is a complex mixture of substances, typically a heterogeneous mixture of compounds for which no single structural formula will suffice. Elemental and spectroscopic characterization of the first component differentiates it from most other humic-based organic complexes, such as Humic and Fulvic Acids, as further discussed below. Blending of individual batches of the first component may be performed to provide consistency and to compensate for the normal variations of a naturally-derived material.

Detailed chemical and biological testing has shown that the complex mixture of substances of the first component is a unique composition both in its biological effect on plants and its chemical composition compared to Humic and Fulvic acids.

Characterization and Methods for the First Component

The organic compounds making up the first component of the composition, can be characterized in a variety of ways (e.g., by molecular weight, distribution of carbon among different functional groups, relative elemental composition, amino acid content, carbohydrate content, etc.). In one aspect, the first component was characterized relative to known standards of humic-based substances.

For purposes of characterizing carbon distribution among different functional groups, suitable techniques include, without limitation, 13C-NMR, elemental analysis, Fourier transform ion cyclotron resonance mass spectroscopy (FTICR-MS) and Fourier transform infrared spectroscopy (FTIR). The chemical characterization of the first component and Humic substance standards were carried out using Electro spray Ionization Fourier Transform Ion Cyclotron Resonance Mass Spectroscopy (ESI-FTICR-MS), Fourier Transform Infrared Spectroscopy (FTIR) and elemental analysis for metals using ICP-AES, conducted by Huffman Laboratories, Inc. and the University of Washington.

Elemental, molecular weight, and spectroscopic characterization of the first component is consistent with an organic complex that consists primarily of lignin and tannin compounds (and mixtures of condensed and un-condensed tannin), condensed aromatics and trace amounts of lipid and inorganics. Thousands of compounds are present, with molecular weights ranging from 225 to 700 daltons, the majority of compounds having between about 10 to about 39 carbon atoms per molecule. The first component is generally composed of carbon, oxygen, and hydrogen, with small amounts of nitrogen, and sulfur. The first component also contains potassium and iron at levels above 5%.

The elemental composition of the dissolved solids typically present in the first component is given in Table A. If the organic compounds are separated from the inorganic elements, the elemental breakdown is: C 55%, H 4%, O 38%, N 1.8%, and S 2.2%.

TABLE A

Average Elemental Composition of dissolved solids in the first component, based upon average values from 10 different lots.

| Element | % |
| --- | --- |
| Carbon | 35.1 |
| Oxygen | 24.6 |
| Hydrogen | 2.5 |
| Sulfur | 2.1 |
| Nitrogen | 1.3 |
| Potassium | 27.3 |
| Iron | 6.1 |
| Calcium | 0.2 |
| Sodium | 0.2 |
| Phosphorous | 0.1 |
| Other | 0.5 |

Among the classes of organic compounds present in the first component, preliminary analysis generally revealed that there were lignin and tannin (mixture of condensed and un-condensed), condensed aromatics, unidentified substances and some lipids present. Each of these classes of compounds were further characterized by a rather narrow Mw range and number of carbons/molecule. The breakdown of the number and percentage of each of the various compound classes, their MW's and carbon atoms/molecule (Carbon Range) for a first representative sampling of the first component is given in Table B1.

TABLE B1

Compound Classes in the first component along with size and carbon ranges for compounds in each class. Based upon composite of 3 different production batches. Results for individual batches are very similar.

| Compound Class | # Compounds | % of Total | Size Range (daltons) | Carbon Range |
|---|---|---|---|---|
| Lignin | 1139 | 57 | 226-700 | 11 to 39 |
| Tannin | 587 | 30 | 226-700 | 10 to 31 |
| Condensed Aromatic | 220 | 11 | 238-698 | 13 to 37 |
| Lipid | 18 | 1 | 226-480 | 14 to 30 |
| Carbohydrate | 1 | 0 | 653 | 24 |
| Other | 23 | 1 | 241-651 | 12 to 33 |

A breakdown of the number and percentage of each of the various compound classes, their MW's and carbon atoms/molecule (Carbon Range) for a second representative sampling based upon an average of 3 different production batches for the first component is given in Table B2.

TABLE B2

Compound Classes in the first component, along with size and carbon ranges for compounds in each class. Based upon average of 3 different production batches. Results for individual batches are very similar.

| Compound Class | # | % of Total | Size Range (daltons) | Carbon Range |
|---|---|---|---|---|
| Lignin | 711 | 56 | 226-700 | 11 to 39 |
| Tannin | 410 | 33 | 226-700 | 10 to 31 |
| Condensed Aromatic | 122 | 10 | 238-698 | 13 to 37 |
| Lipid | 12 | ~1 | 226-480 | 14 to 30 |
| Carbohydrate | 1 | 0 | 653 | 24 |
| Other | 14 | ~1 | 241-651 | 12 to 33 |

Table C, summarizes the oxygen-to-carbon (O/C) and hydrogen-to-carbon (H/C) ratios used in defining the classes described above.

TABLE C

Elemental Ratios and chemical classifications used in characterizing samples of the first component.

| Class | O/C | H/C | Aromaticity Index |
|---|---|---|---|
| Lignin | 0.15-0.6 | 0.6-1.7 | <0.7 |
| Tannin | 0.6-1.0 | 0.5-1.4 | <0.7 |
| Condensed Aromatic | 0.1-0.7 | 0.3-0.7 | >0.7 |
| Lipid | 0-0.2 | 1.8-2.2 | |
| Carbohydrate | 0.6-1.0 | 1.8-2.2 | |

Comparison with Humic Substance Standards

Comparative elemental and structural characterization of Humic Substances verses samples of the first component were performed. Three humic substances standards from the International Humic Substances Society were used: Leonardite Humic Acid (LHA), Pahokee Peat Humic Acid (PPHA), and Suwannee River Fulvic Acid II (SRFA). Each humic substance standard and each sample of the first component was analyzed by FTIR and ESI-FTICR-MS. A portion of each humic substance standard was dissolved in $NH_4OH$/water for the ESI-FTICR-MS analysis. Three samples of the first component (#1, #2, and #3) were prepared for analysis with cation exchange resin (AG MP-50, Bio-Rad Laboratories, Hercules, Calif.). Comparison of the Humic Substance standards and each sample of the first component is presented in Table D.

TABLE D

Comparison of humic substance standards samples of the first component.

| Sample | O/C | H/C | DBE | Avg. MW |
|---|---|---|---|---|
| Suwannee River Fulvic Acid (SRFA) | 0.39 | 1.01 | 12.7 | 445.7 |
| Pahokee Peat Humic Acid (PPHA) | 0.34 | 0.75 | 16.29 | 429.8 |
| Leonardite Humic Acid (LHA) | 0.3 | 0.79 | 15.8 | 423.6 |
| #1 | 0.54 | 0.87 | 13.7 | 472.9 |
| #2 | 0.54 | 0.89 | 13.23 | 456.9 |
| #3 | 0.5 | 0.91 | 13.23 | 455.7 |

Table D indicates that there are major differences between the Humic Substances standards and the samples representing the first component. For example, the O/C ratio is less than 0.4 in all of the Humic Substances but is at least 0.5 for the first component samples. The DBE for the samples is also significantly lower than for the Humic Acid Standards and the average MW is greater.

Based on mass spectral analysis, there are a number of compounds present in the first component samples that are substantially absent or greatly reduced in the Humic Substance standards. In particular, at least one component of the first component may correspond with one or more tannin compounds. By comparison, in the Humic Substance standards, the % of tannin compounds are present in a small amount. For example, in the Fulvic Acid standard and in the Humic Acid standards, both standards are at least 3×-4× less than the % tannins found in the first component samples, as shown in Table E.

TABLE E

Number and % tannins in Humic Substance Standards verses first component samples.

| Sample | # tannins | % of tannin compounds |
|---|---|---|
| Suwannee River Fulvic Acid (SRFA) | 192 | 8.8 |
| Pahokee Peat Humic Acid (PPHA) | 9 | 1.2 |
| Leonardite Humic Acid (LHA) | 22 | 1.2 |
| #1 | 441 | 35.2 |
| #2 | 357 | 34.6 |
| #3 | 432 | 28.3 |

Comparing the Fourier Transform Infrared (FTIR) spectra for the IHSS standards and first component samples, there are similarities, primarily in the region from 1600 to 1800 $cm^{-1}$. In both sets of samples we see a very strong peak at around 1700 $cm^{-1}$ due to the C=O stretch from a carboxyl functional group and a peak in the 1590 to 1630 region which is consistent with a C=C bond from alkenes or aromatics. However, significant differences in the region from 700 to 1450 $cm^{-1}$ are observed. Peaks at 1160 to 1210 are present in all the spectra and are from the C—O bond of alcohols, ethers, esters and acids. The biggest difference is the peak at 870 $cm^{-1}$ in the first component samples, which is absent in the IHSS standards. This peak may be due to the C—H bond of alkenes and aromatics.

Based on the characterization data, the first component may contain relatively small molecules or supramolecular aggregates with a molecular weight distribution of about 300 to about 18,000 daltons. Included in the organic matter from which the mixture of organic molecules are fractionated are various humic substances, organic acids and microbial exudates. The mixture is shown to have both aliphatic and aromatic characteristics. Illustratively, the carbon distribution shows about 35% in carbonyl and carboxyl groups; about 30% in aromatic groups; about 18% in aliphatic groups, about 7% in acetal groups; and about 12% in other heteroaliphatic groups.

In some embodiments, the mixture of compounds in the first component comprises organic molecules or supramolecular aggregates with a molecular weight distribution of about 300 to about 30,000 daltons, for example, about 300 to about 25,000 daltons, about 300 to about 20,000 daltons, or about 300 to about 18,000 daltons.

Characterizing carbon distribution among different functional groups, suitable techniques can be used include without limitation 13C-NMR, elemental analysis, Fourier transform ion cyclotron resonance mass spectroscopy (FTICR-MS) and Fourier transform infrared spectroscopy (FTIR).

In one aspect, carboxy and carbonyl groups together account for about 25% to about 40%, for example about 30% to about 37%, illustratively about 35%, of carbon atoms in the mixture of organic compounds of the first component.

In one embodiment, aromatic groups account for about 20% to about 45%, for example about 25% to about 40% or about 27% to about 35%, illustratively about 30%, of carbon atoms in the mixture of organic compounds of the first component.

In one embodiment, aliphatic groups account for about 10% to about 30%, for example about 13% to about 26% or about 15% to about 22%, illustratively about 18%, of carbon atoms in the mixture of organic compounds of the first component.

In one embodiment, acetal and other heteroaliphatic groups account for about 10% to about 30%, for example about 13% to about 26% or about 15% to about 22%, illustratively about 19%, of carbon atoms in the mixture of organic compounds of the first component.

In one aspect, the ratio of aromatic to aliphatic carbon is about 2:3 to about 4:1, for example about 1:1 to about 3:1 or about 3:2 to about 2:1 in the first component.

In a particular illustrative aspect, carbon distribution in the mixture of organic compounds of the first component is as follows: carboxy and carbonyl groups, about 35%; aromatic groups, about 30%; aliphatic groups, about 18%, acetal groups, about 7%; and other heteroaliphatic groups, about 12%.

Elemental composition of the organic compounds of the first component is independently in one series of embodiments as follows, by weight: C, about 28% to about 55%, illustratively about 38%; H, about 3% to about 5%, illustratively about 4%; O, about 30% to about 50%, illustratively about 40%; N, about 0.2% to about 3%, illustratively about 1.5%; S, about 0.2% to about 4%, illustratively about 2%.

Elemental composition of the organic compounds of the first component is independently in another series of embodiments as follows, by weight: C, about 45% to about 55%, illustratively about 50%; H, about 3% to about 5%, illustratively about 4%; O, about 40% to about 50%, illustratively about 45%; N, about 0.2% to about 1%, illustratively about 0.5%; S, about 0.2% to about 0.7%, illustratively about 0.4%.

In a particular illustrative aspect, elemental distribution is, by weight: C, about 38%; H, about 4%; O, about 40%; N, about 1.5%; and S, about 2%. The balance consists mainly of inorganic ions, principally potassium and iron in the first component.

In another particular illustrative aspect, elemental distribution is, by weight: C, about 50%; H, about 4%; O, about 45%; N, about 0.5%; and S, about 0.4% in the first component.

Among classes of organic compounds that can be present in the first component are, in various aspects, amino acids, carbohydrates (monosaccharides, disaccharides and polysaccharides), sugar alcohols, carbonyl compounds, polyamines, lipids, and mixtures thereof. These specific compounds typically are present in minor amounts, for example, less than 5% of the total % of compounds.

Examples of amino acids that can be present include without limitation arginine, aspartic acid, glutamic acid, glycine, histidine, isoleucine, serine, threonine, tyrosine and valine.

Examples of monosaccharide and disaccharide sugars that can be present include without limitation glucose, galactose, mannose, fructose, arabinose, ribose and xylose.

Based on the above chemical, elemental and structural characterization, the first component is chemically and biologically unique from Humic and Fulvic acids or combinations thereof. Further, as a result of the nature and extent of gene regulation and over all effect of the first component with respect to improved plant health, drought and salinity stress resistance, it is generally believed that the first component is unique to that of known humic and/or fulvic acid compositions and treatments, for which such activity and properties are generally lacking in quality and quantity. Other beneficial plant function attributes of the first component may be present or result from the methods of treatment and/or the gene regulation obtained from the first component.

Without being bound by theory, it is believed that at least the ability of the first component to complex ions assists in plant nutrition by facilitating uptake and/or translocation of ions in the plant. Facilitating uptake and/or translocation of ions may occur through preferential movement of ions via the xylem or phloem to the growing and fruiting points of the plant. Alternatively, or in combination with the above, facilitating uptake and/or translocation of ions may occur through regulation of one or more genes related to ion transport or other biological function of the plant or seed. Facilitating uptake and/or translocation of ions may occur through absorption and transport via the seed coat of the pre- or post-planted seed. Inorganic ions can be positively charged cations or negatively charged anions. Examples of inorganic cations include $Mg^{2+}$, $Ca^{2+}$, $Mn^{2+}$, $Fe^{2+}$ and $Fe^{3+}$. Examples of inorganic anions include borate and silicate. Such reversible binding or complexing may take the form of chelation or by ionic or non-ionic interaction. Other abilities of the first component to assists in plant nutrition can be present or employed.

A suitable mixture of organic compounds can be found, for example, as one of many components in products marketed as Carbon Boost-S soil solution and KAFE™-F foliar solution of Floratine Biosciences, Inc. (FBS). Information on these products is available at www.fbsciences.com. Thus, exemplary compositions of aspects disclosed and described herein can be prepared by adding to Carbon Boost™-S or KAFE™-F foliar solution as the first component, at least one pesticide as the second component, to a suitable volume of water. In one aspect, the active ingredient is CAS Reg. No. 1175006-56-0, and corresponds, by way of example, to the first component.

The amount of the first component that should be present in the composition depends on the particular organic mixture used. The amount should not be so great as to result in a physically unstable composition, for example by exceeding the limit of solubility of the mixture in the composition, or by causing other essential components to fall out of solution. On the other hand, the amount should not be so little as to fail to provide enhanced nutrition, growth, enhanced stress resistance, or enhanced disease protection when applied to a target plant species. For any particular organic mixture, one of skill in the art can, by routine formulation stability and bioefficacy testing, optimize the amount of organic mixture in the composition for any particular use.

Particularly where a mixture of organic compounds, as found, for example, in the commercially available formulations sold under the tradenames Carbon Boost™-S and KAFET™-F, is used, the amount of the first component needed in a nutrition composition will often be found to be remarkably small. For example, as little as one part by weight (excluding water) of such a mixture can, in some circumstances, assist in foliar delivery of up to about 1000 or more parts by weight of the second component to a site of deposition in a plant. In other circumstances, it may be found beneficial to add a greater amount of the organic mixture, based on routine testing. Typically, a suitable ratio of the first component to the second component is about 1:2000 to about 1:5, for example about 1:1000 to about 1:10 or about 1:500 to about 1:20, illustratively about 1:100. If using Carbon Boost™-S or KAFE™-F solution as the source of organic compounds, a suitable amount of such solution to be included in a concentrate composition of second component herein is about 1 part by weight Carbon Boost™-S or KAFE™-F solution in about 5 to about 25, for example about 8 to about 18, illustratively about 12, parts by weight of the concentrate composition.

Optionally, additional components can be present in a composition of the present invention together with the first and second components as describe above. For example, the composition can further comprise as a third component at least one agriculturally acceptable source of a plant nutrient other than those used as the first and second component. Additional sources of these nutrients can be present, if desired.) Examples of other plant nutrients, sources of which can optionally be included, are potassium (K), and sulfur (S), phosphorus (P), calcium (Ca), magnesium (Mg), iron (Fe), zinc (Zn), manganese (Mn), copper (Cu) and boron (B).

Advantageously, addition of multivalent cations such as $Ca^{+2}$, $Mg^{+2}$, $Mn^{+2}$, or $Fe^{+2/3}$ to an aqueous composition containing the first component and a pesticide generally known to complex with the multivalent cations such as Ca, Mg, Mn, or Fe can substantially maintain the potency of the pesticide compared to a solution comprising the multivalent cations and pesticide in the absence of the first component.

For example, it is generally known that glyphosate effectiveness is reduced when combined in an aqueous solution comprising of multivalent cations such as $Mn^{+2}$. Thus, it may be required to treat the plant or its locus with separate applications of the herbicide and the nutrient. The first component provides for the direct mixing (single tank) of herbicide/multivalent cation nutrients such as $Ca^{+2}$, $Mg^{+2}$, $Mn^{+2}$, or $Fe^{+2/3}$, for example, glyphosate and $Mn^{+2}$, as further described below.

Other ingredients can optionally be present in a composition disclosed and described herein, including such conventional formulation adjuvants as surfactants (for example to enhance wetting of leaf surfaces), spray drift controlling agents, antifoam agents, viscosity modulating agents, antifreezes, coloring agents, etc. Any of these can be added if desired, so long as they do not destabilize essential components of the composition.

Processes for preparing a composition disclosed and described herein typically involve simple admixture of the required ingredients. If desired, any of the ingredients can be pre-dissolved in a suitable volume of water before mixing with other ingredients. Order of addition is not generally critical.

Second Component

The second component can be a pesticide, where the term "pesticide" herein refers to at least one herbicide, insecticide, fungicide, bactericide, anti-viral, plant nutrient, or a combination thereof.

Herbicides can include, for example, any herbicide that is effective for the control or remediation of weeds, for example imidazolinone, sulfonylurea, glyphosate, glufosinate, L-phosphinothricin, triazine, benzonitrile and combinations thereof. Herbicides also include Dicamba (3,6-dichloro-o-anisic acid or 3,6-dichloro-2-methoxybenzoic acid), the active ingredient in herbicides such as Banvel.™, (BASF), Clarity™, (BASF), and Vanquish™ (Syngenta).

Insecticides can include, for example, any insecticide that is effective for the control or remediation of insects, and include ovicides and larvicides. Exemplary insecticides include organochlorines, organophosphates, carbamates, neonicotinoids, phenylpyrazoles, and pyrethroids, for example tefluthrin, terbufos, cypermethrin, thiodicarb, lindane, furathiocarb, acephate, butocarboxim, carbofuran, NTN, endosulfan, fipronil, diethion, aldoxycarb, methiocarb, oftanol, (isofenphos), chlorpyrifos, bendiocarb, benfuracarb, oxamyl, parathion, capfos, dimethoate, fonofos, chlorfenvinphos, cartap, fenthion, fenitrothion, HCH, deltamethrin, malathion, disulfoton, and combinations thereof. In one aspect, the second component comprises an insecticidally effective amount of at least one neonicotinoid or phenylpyrazole insecticide, and combinations thereof.

Fungicides can include, for example any fungicide that is effective for the control of fungi and oomycetes, such as, those effective for the control or remediation of the phytopathogenic fungi belonging to the Ascomycetes (*Fusarium* spp., *Thielaviopsis* spp., *Verticillium* spp., *Magnaporthe grisea*), Basidiomycetes (*Rhizoctonia* spp., *Phakospora pachyrhizi* Sydow, *Puccinia* spp.); and Oomycetes (*Phytophthora, Pythium* spp., *Phytophthora* spp.). Exemplary fungicides include Benomyl (also known as Benlate), Bitertanol, Captan, Carbendazim, Carboxin (also known as Carbathiin), Capropamid, Cymoxanil, Cyprodinil, Difenoconazole, Ethirimol, Fenpiclonil, Fenpropimorph, Fludioxonil, Fluquinconazole, Flutolanil, Flutriafol, Fosetyl-aluminum, Fuberidazole, Guazatine, Hymexanol, Kasugamycin, Imazalil, Imibenconazole, Iminoctadine-triacetate, Ipconazole, Iprodione, Mancozeb, Maneb, Mepronil, Metalaxyl, Metalaxyl-M (Mefenoxam), Metconazole, Metiram, MON 65500 (Silthiopham-ISO proposed), Myclobutanil, Nuarimol, Oxadixyl, Oxine-copper, Oxolinic acid, Perfurazoate, Pencycuron, Prochloraz, Propamocarb hydrochloride, Pyroquilon, Quintozene (also known as PCNB), Silthiopham—see MON 65500, Tebuconazole, Tecnazene, Tetraconazole, Thiabendazole, Thifluzamide, Thiophenate-methyl, Thiram, Tolclofos-methyl, Triadimenol, Triazoxide, Triflumizole, Triticonazole, and combinations thereof. In one aspect, the second component comprises a fungicidally effective amount of at least two fungicides including at least one phenylamide (acylalanine type), at least one phenylpyrrole, and at least one triazole. In another aspect, the second component comprises a fungicidally effective amount of at least three fungicides including at least one phenylamide (acylalanine type), at least one phenylpyrrole, and at least one triazole. In one aspect, the fungicide is selected from the family of strobilurins, for example, Quadris™ (Syngenta) Headline™ (BASF) and Stratego™ (Bayer).

Bactericides can include, for example, any bactericides that are effective for the control or remediation of *Agrobacterium, Burkholderia, Proteobacteria* (e.g., *Xanthomonas* spp. and *Pseudomonas* spp.) Phytoplasma, and Spiroplasma.

Anti-viral agents can include, for example, agents that are effective for the control or remediation of asymptomatic viruses, protozoa and parasitic plants. Nematicides, for example abamectin, can be used as a nematode seed treatment.

In one aspect, the second component comprises a combination of an insecticidally effective amount of at least one neonicotinoid or phenylpyrazole insecticide and a fungicidally effective amount of at least one fungicide selected from phenylamide (acylalanine type), phenylpyrrole or triazole. In one specific aspect, the second component comprises a combination of an insecticidally effective amount of at least one neonicotinoid or phenylpyrazole insecticide and a fungicidally effective amount of at least three fungicides including at least one phenylamide (acylalanine type), at least one phenylpyrrole, and at least one triazole.

The second component can also include growth regulators, for example, cytokinins, auxins, gibberellins, and combinations thereof.

The second component can also comprise one or more plant macronutrients or plant micronutrients. The term "macronutrient" can refer to an element for plant growth which is utilized by plants in proportionally larger amounts relative to micronutrients. The term "micronutrients" refers to an element utilized by plants during growth which are used in smaller amounts relative to macronutrients. For example, plant macronutrients include nitrogen, potassium, phosphorus, calcium, magnesium and sulfur. The second component can comprise various combinations and relative amounts of individual macronutrients. For example, plant micronutrients include iron, manganese, zinc, copper, boron, molybdenum and cobalt. Numerous compounds and substances are available to provide micronutrients as the second component. Various combinations and relative amounts of micronutrients can be utilized in the second component.

The second component can also include, in addition to any of the above, a mold inhibitor, an absorbant, a penetrant, and combinations thereof.

Methods

Methods of use of the composition as described herein for seed treating, nutrition and/or for reducing susceptibility to disease of a plant are further disclosed. The composition can be applied to a single plant (e.g., a houseplant or garden ornamental) or to an assemblage of plants occupying an area. In some embodiments, the composition is applied to an agricultural or horticultural crop, more especially a food crop. A "food crop" herein means a crop grown primarily for human consumption. Methods of the present invention are appropriate both for field use and in protected cultivation, for example, greenhouse use.

While the present methods can be beneficial for gramineous (belonging to the grass family) crops such as cereal crops, including corn, wheat, barley, oats and rice, they are also highly appropriate for non-gramineous crops, including vegetable crops, fruit crops, broad-leaved field crops such as soybeans, seed crops or a crop of any species grown specially to produce seed. The terms "fruit" and "vegetable" herein are used in their agricultural or culinary sense, not in a strict botanical sense; for example, tomatoes, cucumbers and zucchini are considered vegetables for present purposes, although botanically speaking it is the fruit of these crops that is consumed.

Vegetable crops for which the present methods can be found useful include without limitation:

leafy and salad vegetables such as amaranth, beet greens, bitterleaf, bok choy, Brussels sprout, cabbage, catsear, celtuce, choukwee, Ceylon spinach, chicory, Chinese mallow, chrysanthemum leaf, corn salad, cress, dandelion, endive, epazote, fat hen, fiddlehead, fluted pumpkin, golden samphire, Good King Henry, ice plant, jambu, kai-lan, kale, komatsuna, kuka, Lagos bologi, land cress, lettuce, lizard's tail, melokhia, mizuna greens, mustard, Chinese cabbage, New Zealand spinach, orache, pea leaf, polk, radicchio, rocket (arugula), samphire, sea beet, seakale, Sierra Leone bologi, soko, sorrel, spinach, summer purslane, Swiss chard, tatsoi, turnip greens, watercress, water spinach, winter purslane and you choy;

flowering and fruiting vegetables such as acorn squash, Armenian cucumber, avocado, bell pepper, bitter melon, butternut squash, caigua, Cape gooseberry, cayenne pepper, chayote, chili pepper, cucumber, eggplant (aubergine), globe artichoke, luffa, Malabar gourd, parwal, pattypan squash, perennial cucumber, pumpkin, snake gourd, squash (marrow), sweetcorn, sweet pepper, tinda, tomato, tomatillo, winter melon, West Indian gherkin and zucchini (courgette);

podded vegetables (legumes) such as American groundnut, azuki bean, black bean, black-eyed pea, chickpea (garbanzo bean), drumstick, dolichos bean, fava bean (broad bean), French bean, guar, haricot bean, horse gram, Indian pea, kidney bean, lentil, lima bean, moth bean, mung bean, navy bean, okra, pea, peanut (groundnut), pigeon pea, pinto bean, rice bean, runner bean, soybean, tarwi, tepary bean, urad bean, velvet bean, winged bean and yardlong bean;

bulb and stem vegetables such as asparagus, cardoon, celeriac, celery, elephant garlic, fennel, garlic, kohlrabi, kurrat, leek, lotus root, nopal, onion, Prussian asparagus, shallot, Welsh onion and wild leek;

root and tuber vegetables, such as ahipa, arracacha, bamboo shoot, beetroot, black cumin, burdock, broadleaf arrowhead, camas, canna, carrot, cassava, Chinese artichoke, daikon, earthnut pea, elephant-foot yam, ensete, ginger, gobo, Hamburg parsley, horseradish, Jerusalem artichoke, jicama, parsnip, pignut, plectranthus, potato, prairie turnip, radish, rutabaga (swede), salsify, scorzonera, skirret, sweet potato, taro, ti, tigernut, turnip, ulluco, wasabi, water chestnut, yacon and yam; and herbs, such as angelica, anise, basil, bergamot, caraway, cardamom, chamomile, chives, cilantro, coriander, dill, fennel, ginseng, jasmine, lavender, lemon balm, lemon basil, lemongrass, marjoram, mint, oregano, parsley, poppy, saffron, sage, star anise, tarragon, thyme, turmeric and vanilla.

Fruit crops for which the present methods can be found useful include without limitation apple, apricot, banana, blackberry, blackcurrant, blueberry, boysenberry, cantaloupe, cherry, citron, clementine, cranberry, damson, dragonfruit, fig, grape, grapefruit, greengage, gooseberry, guava, honeydew, jackfruit, key lime, kiwifruit, kumquat, lemon, lime, loganberry, longan, loquat, mandarin, mango, mangosteen, melon, muskmelon, orange, papaya, peach, pear, persimmon, pineapple, plantain, plum, pomelo, prickly pear, quince, raspberry, redcurrant, starfruit, strawberry, tangelo, tangerine, tayberry, ugli fruit and watermelon.

Seed crops, for example, specialized crops used to produce seed of any plant species, for which the present methods can be found useful include, in addition to cereals (e.g., barley, corn (maize), millet, oats, rice, rye, sorghum (milo) and wheat), non-gramineous seed crops such as buckwheat, cotton, flaxseed (linseed), mustard, poppy, rapeseed (including canola), safflower, sesame and sunflower.

Other crops, not fitting any of the above categories, for which the present methods can be found useful include without limitation sugar beet, sugar cane, hops and tobacco.

Each of the crops listed above has its own particular nutrition and disease protection needs. Further optimization of compositions described herein for particular crops can readily be undertaken by those of skill in the art, based on the present disclosure, without undue experimentation.

Methods of using the compositions disclosed and described herein comprise applying a composition as described herein to a seed, to a foliar surface of a plant, or to a locus of the plant or seed.

The term "agriculturally acceptable" applied to a material or composition herein means not unacceptably damaging or toxic to a plant or its environment, and not unsafe to the user or others that may be exposed to the material when used as described herein.

A "foliar surface" herein is typically a leaf surface, but other green parts of plants have surfaces that may permit absorption of active ingredient, including petioles, stipules, stems, bracts, flowerbuds, etc., and for present purposes "foliar surfaces" will be understood to include surfaces of such green parts.

A "locus" as used herein is inclusive of a foliar surface and also includes an area in proximity to a plant or the area in which a plurality of seed is or can be sown.

"Seed treatment" as used herein refers generally to contacting a seed with a compound or composition of matter containing or comprising at least one active ingredient (a.i. or AI). The compound or composition of matter may be in any form suitable to the seed, for example, liquid, gel, emulsion, suspension, dispersion, spray, or powder. Seed treatment is inclusive of seed coating and seed dressing.

"Seed coating" or "seed dressing" as used herein refers generally to a coating or matrix formed on at least part of the seed, the coating or matrix containing or comprising the at least one AI. Optional compounds or agents may be included in the seed coating to facilitate the seed coating process or the disintegration/releasing of the at least one AI from the coating, or to prevent excessive dust-off or to add color to the treated seed.

The term "seed" as used herein, is not limited to any particular type of seed and can refer to seed from a single plant species, a mixture of seed from multiple plant species, or a seed blend from various strains within a plant species. The disclosed and described compositions can be utilized to treat gymnosperm seed, dicotyledonous angiosperm seed and monocotyledonous angiosperm seed.

Compositions disclosed and described herein can be applied using any conventional system for applying liquid or solid to a seed or foliar surface or locus. Most commonly, application by spraying will be found most convenient, but other techniques, including application by tumbling, brush or by rope-wick can be used if desired. For spraying, any conventional atomization method can be used to generate spray droplets, including hydraulic nozzles and rotating disk atomizers. Introduction of the composition into an irrigation system can be used.

For foliage surface or locus applications, the application rate of the composition can be between about 0.01 gram/hectare to about 10.0 gram/hectare dry weight, between about 0.2 gram/hectare to about 2.0 gram/hectare dry weight, between 0.3 gram/hectare to about 1.5 gram/hectare dry weight, or between about 0.4 gram/hectare to about 1.0 gram/hectare dry weight applied in the soil or as a foliar application to the foliage or the locus of the plant.

Compositions disclosed and described herein can be provided in concentrate form, (e.g., liquid, gel, or reconstitutable powder form), suitable for further dilution and/or mixing in water prior to application to the seed, plant, or locus. Alternatively, they can be provided as a ready-to-use solution for direct application. Because compositions disclosed and described herein can be combined with other fertilizer solutions and/or with pesticide solutions, they can be diluted and/or reconstituted by mixing with such other solutions.

The above concentrate compositions are suitable for further dilution. For application to plant foliage, a concentrate composition can be diluted up to about 600-fold or more with water, more typically up to about 100-fold or up to about 40-fold. Illustratively, a concentrate product can be applied at about 0.1 to about 30 l/ha, for example about 5 to about 25 l/ha, in a total application volume after dilution of about 60 to about 600 l/ha, for example about 80 to about 400 l/ha or about 100 to about 200 l/ha.

For seed treatment applications, a concentrate composition can be diluted up to about 600-fold or more with water, more typically up to about 100-fold or up to about 40-fold. Illustratively, a concentrate product can be applied at about 0.1 mg/Kg seed to about 100 mg/Kg seed, for example about 0.1 mg/Kg seed, 0.5 mg/Kg seed, 0.75 mg/Kg seed, 1.0 mg/Kg seed, 1.25 mg/Kg seed, 1.5 mg/Kg seed, 1.75 mg/Kg seed, 2.0 mg/Kg seed, 2.5 mg/Kg seed, 3.0 mg/Kg seed, 3.5 mg/Kg seed, 4.0 mg/Kg seed, 4.5 mg/Kg seed, 5.0 mg/Kg seed, 5.5 mg/Kg seed, 6.0 mg/Kg seed, 6.5 mg/Kg seed, 7.0 mg/Kg seed, 7.5 mg/Kg seed, 8.0 mg/Kg seed, 8.5 mg/Kg seed, 9.0 mg/Kg seed, 9.5 mg/Kg seed, and 10.0 mg/Kg seed. A concentrate product can also be applied at about 15 mg/Kg, 20 mg/Kg, 25 mg/Kg, and 30 mg/Kg.

Application solutions prepared by diluting concentrate compositions as described above represent further aspects of the compositions and methods disclosed and described herein.

Seed Treatments and Seed Coatings

In one aspect, methods of promoting healthy growth of plant seeds is provided that comprises contacting the seeds with an aqueous composition comprising the first component and optionally a second component selected from one or more pesticides and/or one or more natural plant hormones. The seeds may be contacted with the aqueous composition by conventional means such as spraying, rolling, or tumbling. Thus, the first component can be combined with a second component selected from pesticides, for example, Fipronil and other fluorocyanobenpyrazoles, strobilurins, tebuconazole, a broad-spectrum fungicide treatment that protects against wide range of diseases in cereal grains, soybeans, and other crops as well as other members of the class of azoles; thiram, a fungicide treatment for control of damping-off, *Phytophthora*, and other soil-borne diseases effective in a broad range of crops; myclobutanil, a fungicide effect for sore shin and black root rot in cotton; imidacloprid and other neonicotinoids, effective for systemic, early-season insect control; metalaxyl, for systemic control of *Pythium* and *Phytophthora*: combinations of pesticides such as tebuconazole and metalaxyl; and tebuconazole, imidacloprid and metalaxyl; imazapyr (StrigAway®) to provide effective protection against Striga; zinc ions, copper ions, manganese ions, or combinations thereof (e.g., Zn+Cu, Zn+Mn); glyphosate. Combinations of the first component and the pesticide can be mixed in aqueous media at a concentration, and brought into contact with the seeds for a time sufficient to provide improved plant health and/or growth.

In one particular aspect, an effective seed treatment or foliar treatment comprises a seed treated or foliar surface with a combination comprising the first component and glyphosate.

In another particular aspect, an effective seed treatment comprises a seed treated with a combination comprising the first component, glyphosate, and a $Mn^{+2}$ and/or $Zn^{+2}$ ion source.

In another particular aspect, an effective seed treatment comprises a seed treated with a combination comprising the first component and second component comprising a plant growth hormone. The plant growth hormone can be from the class of abscisic acid, auxins, cytokinins, gibberellins, brassinolides, salicyclic acid, jasmonates, plant peptides, polyamines, and stringolactones.

In another aspect, methods of promoting healthy growth of plant seeds is provided that comprises applying to the seeds a coating or dressing of a polymer or other matrix, the polymer or matrix comprising the first component and optionally one or more pesticides and/or one or more natural plant hormones. The polymer or matrix is capable of releasing the first component and optionally one or more pesticides and/or one or more natural plant hormones (collectively, "the actives"). The polymer or matrix can be designed to release the actives in response to temperature, moisture content, sunlight, time, or combinations thereof. The polymer or matrix can quickly dissolve or disintegrate releasing the actives or can controllable release the actives over time or in response to a predetermined condition such as temperature, moisture content, sunlight, time, or combinations thereof. The polymer or matrix can be multi-layer, with discrete layers, for example, for disrupting the coating to allow moisture ingress, housing the actives, etc. Suitable polymers or matrixes include hydrogels, microgels, or sol-gels. Specific materials and methods of coatings seeds useful in this regard include such process and materials as used, for example, Intellicoat™ (Landec Inc., Indiana); ThermoSeed™ (Incotec, Netherlands) CelPril™ (Bayer CropScience); ApronMaxx™ (Syngenta); and Nacret™ (Syngenta). The actives can be provided as nanoparticles and incorporated into the polymer or matrix, or directly adhered to the seed coat. The thickness of the polymer or matrix coating may be between from about 0.01 mils to about 10 mils in thickness. The coating can further provide protection for the seeds from mechanical and environmental damages.

For seed treatment or seed coatings as described above, the amount of the first component can be about 0.01 mg/kg seed weight to about 30 mg/kg seed weight. After an initial application of the first component as a seed treatment, it has been found advantageous to apply one or more subsequent soil and/or foliar applications of the first component, for example, after emergence. Application frequency can be, for example, a single application, or up to four applications per season. In certain situations, a single application will suffice. In other situations, the first and/or second and/or third and/or fourth application may precede, supersede, or correspond to a particular growth cycle of the plant, or a known life cycle or endemic habit of an insect, parasite, or undesirable plant species.

First Component Compositions for Plant Health

Methods as described in detail above are useful for nutrition of a plant. Any benefit of enhanced nutrition can be a benefit of the present methods, including without limitation higher quality produce, improved growth and/or a longer growing season (which in either case can lead to higher yield of produce), improved plant stress management including increased stress tolerance and/or improved recovery from stress, increased mechanical strength, improved root development, improved drought resistance and improved plant health. Combinations of benefits can be obtained. It has been observed that seeds and/or plants contacted with the first component emerge faster and have significantly increased chlorophyll production, greatly improved cold resistance, and improved water log resistance compared to seeds or plants not contacted with the first component.

In various embodiments, yield of produce can be increased, for example by at least about 2%, at least about 4%, at least about 6%, at least about 8%, at least about 10%, at least about 15%, at least about 25% or at least about 50%, over plants not receiving a nutrient treatment comprising the first component.

Improved plant health, particularly resistance to or protection from disease, especially bacterial or fungal disease, is an important benefit of methods disclosed and described herein. In one embodiment, a method is provided for reducing susceptibility of a plant to insect, fungal or bacterial disease. "Reduced susceptibility" herein includes reduced incidence of fungal or bacterial infection and/or reduced impact of such infection as occurs on the health and growth of the plant. It is believed, without being bound by theory, that the enhanced nutrition afforded by compositions disclosed and described herein strengthens the plant's natural defenses against fungal and bacterial pathogens. Examples of such pathogens include, without limitation, *Alternaria* spp., *Blumeria graminis, Bottytis cinerea, Cochliobolus miyabeanus, Colletotrichum gloeosporioides, Diplocarpon rosae, Fusarium oxysporum, Magnaporthe grisea, Magnaporthe salvinii, Phaeosphaeria nodorum, Pythium aphanidermatum, Pythium ultimum, Sclerotinia homoeocarpa, Septoria nodorum, Sphaerotheca pannosa, Sphaerotheca xanthii, Thanatephorus cucumeris* and *Uncinula necator.*

A single species of pathogen can cause a variety of different diseases in different crops. Examples of bacterial and fungal diseases of plants include, without limitation, *anthracnose, armillaria, ascochyta, aspergillus*, bacterial blight, bacterial canker, bacterial speck, bacterial spot, bacterial wilt, bitter rot, black leaf, blackleg, black rot, black spot, blast, blight, blue mold, *botrytis*, brown rot, brown spot, *cercospora*, charcoal rot, *cladosporium*, clubroot, covered smut, crater rot, crown rot, damping off, dollar spot, downy mildew, early blight, ergot, *erwinia*, false loose smut, fire blight, foot rot, fruit blotch, *fusarium*, gray leaf spot, gray mold, heart rot, late blight, leaf blight, leaf blotch, leaf curl, leaf mold, leaf rust, leaf spot, mildew, necrosis, *peronospora, phoma*, pink mold, powdery mildew, *rhizopus*, root canker, root rot, rust, scab, smut, southern blight, stem canker, stem rot, *verticillium*, white mold, wildfire and yellows.

As early as 1999, genetically modified (GM) plants, for example, glyphosate-resistant soybean, when compared to the top conventional varieties, provided a lower yield (sometimes referred to as "yield drag"). Such patterns were observed when other traits were introduced into soybeans by conventional breeding. While it may not be attributable to the glyphosate-resistant trait or the GM nature of the crop, there is evidence, suggesting manganese deficiency in some glyphosate-resistant plants, may contribute to this effect. Attempts to circumvent the glyphosate-resistant plant's manganese deficiency have been hindered by lower herbicidal performance of the glyphosate. At least one theory attributes the decline in glyphosate performance when physically blended with sources of metal ions to chelation of metal ion by the glyphosate, and hence a decrease in the overall effectiveness of a given concentration of glyphosate.

As discussed above, the first component can be mixed with glyphosate and multivalent metal cations without significant decrease in the effectiveness of the herbicide and/or decrease the effectiveness of the uptake of metal cation. While it may be that the first component is disrupting the complexation or chelation of the metal cations with the glyphosate, it is generally believed, without being bound to any particular theory, that the first component regulates at least one gene associated with ion transport of the target plant such that the effectiveness of the glyphosate is maintained and/or the uptake of the metal cation is maintained relative to a composition of glyphosate/metal cation without the first component. This is possible even though the total available concentration of the glyphosate is effectively reduced from interaction with the metal cation. As a result, the amount of metal cation sensitive herbicide glyphosate need not be increased in application rate or can be reduced when used in combination with the first component and optionally, the multivalent metal cations.

EXPERIMENTAL EXAMPLES

Experiment 1

Enhanced Seed Germination

Three different crops (corn, soybean, and canola) were evaluated. In each experiment, 50 seeds were placed on sponges which had been soaked with 500 ml of water (the Control) or with 500 ml water that contained varying amounts of the first component. The first component concentrations varied from 0.6 mg A.I./Kg solution to 12 mg A.I./Kg. After seeds were placed on the sponges, they were placed in a dark growth chamber at 22° C. and the number of seeds which had germinated was determined every 24 hours until 90% of the seed had germinated or 120 hours, whichever came first. Germination results are shown in Tables 1-3.

TABLE 1

Canola Germination of control vs contact with first component.

| First Component Treatment | Time (hours) | | | | |
|---|---|---|---|---|---|
| | 24 | 48 | 72 | 96 | 120 |
| Corn Control | 0% | 7% | 20 | 35 | 47 |
| 0.6 mg/Kg Corn seed | 0% | 9 | 38 | 75 | 77 |
| 1.2 mg/Kg Corn seed | 0% | 11 | 36 | 60 | 66 |
| 6.0 mg/Kg Corn seed | 0% | 11 | 24 | 69 | 71 |
| 12.0 mg/Kg Corn seed | 0% | 12 | 32 | 51 | 58 |

TABLE 2

Soybean Germination of control vs contact with first component.

| First Component Treatment | Time (hours) | | | | |
|---|---|---|---|---|---|
| | 24 | 48 | 72 | 96 | 120 |
| Soybean Control | 0% | 0% | 4% | 18% | 81% |
| 0.6 mg/Kg Soybean seed | 0% | 0% | 24% | 44% | 90% |
| 1.2 mg/Kg Soybean seed | 0% | 0% | 24% | 46% | 96% |
| 6.0 mg/Kg Soybean seed | 0% | 0% | 17% | 40% | 93% |
| 12.0 mg/Kg Soybean seed | 0% | 0% | 16% | 38% | 96% |

TABLE 3

Corn Germination of control vs contact with first component.

| First Component Treatment | Time (hours) | | | | |
|---|---|---|---|---|---|
| | 24 | 48 | 72 | 96 | 120 |
| Corn Control | 0% | 0% | 4% | 18% | 81% |
| 0.6 mg/Kg Corn seed | 0% | 0% | 5% | 65% | 100% |
| 1.2 mg/Kg Corn seed | 0% | 0% | 10% | 60% | 95% |
| 6.0 mg/Kg Corn seed | 0% | 0% | 10% | 65% | 95% |
| 12.0 mg/Kg Corn seed | 0% | 0% | 20% | 70% | 95% |

The results demonstrate the enhanced germination rate of a variety of crop seeds after contacting with the first component.

Experiment 2

First Component Application Rate Study

The purpose of this experiment was to evaluate the effect of varying rates of the first component on seed germination. Three different crops (wheat, rice, and canola) were evaluated. The experiment was set up as a randomized complete block design with treatment rates that ranged from 0.039 mg A.I./kg of seed to 1.56 mg A.I./kg of seed.

A total of 20 seeds were grown in small soil filled plastic trays. The trays were filled with a 30:60 mixture of a commercial granular ceramic amendment from the golf course green's construction industry called PermO$^2$Pore and 0.1 mm sand. Small holes were punched under each tray to allow for drainage. This soil mixture has been shown in previous experiments to provide an ideal balance of water holding capacity, drainage and air exchange. The seeds were treated with water and A.I. so that the total spray volume was identical for all seed. After treatment, the seeds were placed on the growth medium and placed in a dark growth chamber at 22° C. The number of seeds which had germinated was determined every 24 hours until 90% of the seed had germinated or 120 hours, whichever came first. Germination results (number of seeds of the 20 seeds that germinated) are summarized below in Tables 3, 4, and 5.

TABLE 4

Wheat Germination Rate of control vs contact with first component.

| First Component Treatment | Time (hours) | | |
|---|---|---|---|
| | 24 | 48 | 96 |
| Untreated Wheat Control | 13.5 | 17.3 | 17.8 |
| 0.039 mg/Kg Wheat seed | 16.0 | 18.5 | 19.0 |
| 0.156 mg/Kg Wheat seed | 17.5 | 18.5 | 18.8 |
| 0.312 mg/Kg Wheat seed | 15.3 | 18.5 | 18.5 |
| 1.56 mg/Kg Wheat seed | 12.8 | 16.8 | 17.8 |

TABLE 5

Rice Germination Rate of control vs contact with first component.

| First Component Treatment | Time (hours) | | |
|---|---|---|---|
| | 72 | 96 | 120 |
| Untreated Rice Control | 3 | 8.3 | 12.3 |
| 0.039 mg/Kg Rice seed | 7.8 | 13.5 | 14.5 |
| 0.156 mg/Kg Rice seed | 13.0 | 16.5 | 17.5 |
| 0.312 mg/Kg Rice seed | 9.5 | 13.5 | 15.5 |
| 1.56 mg/Kg Rice seed | 7.3 | 11.3 | 13.8 |

TABLE 6

Canola Germination Rate of control vs contact with first component.

| First Component Treatment | Time (hours) | | | |
|---|---|---|---|---|
| | 24 | 36 | 48 | 96 |
| Untreated Canola Control | 8.8 | 17.5 | 18.3 | 19.8 |
| 0.039 mg/Kg Canola seed | 12.0 | 18.0 | 18.0 | 19.0 |
| 0.234 mg/Kg Canola seed | 11.8 | 18.8 | 19.5 | 19.5 |
| 1.56 mg/Kg Canola seed | 10.3 | 17.0 | 17.8 | 18.8 |

This experiment demonstrated that first component as an A.I. applied directly to seed increased the germination rate of all three crops, and increased total number of germinated seed for wheat and rice. The temperature in the growth chamber was nearly optimum for the wheat and canola to germinate, but was sub-optimal for the rice which demonstrates the effect of A.I. in mitigating stress that impacts seed germination.

Experiment 3

Clearfield Rice Germination

The purpose of this experiment was to evaluate the first component as an A.I. as a seed treatment to improve germination of two Clearfield Rice Varieties of hybrid rice (CL 111 and CL 151). For both varieties there was an Untreated Control and two application rates of A.I., 3.12 mg A.I./kg of seed and 0.312 mg A.I./kg of seed, respectively. The trial was set up with a Randomized Complete Block design with three replicates per treatment. Each replicate consisted of 25 seed on a sponge. Seeds were treated with A.I. and allowed to dry, and then the seeds were placed on a sponge, which was kept wet with deionized water and the sponge was kept at 20° C. Grains of rice were evaluated once every 24 hours under a binocular microscope to determine the number of germinated seeds per sponge. Grains were counted as germinated when the first shoot pierced the outer husk. Data showing the germination with time for each variety are shown below in Tables 7 and 8.

TABLE 7

Rice Variety CL 111 Germination Rate of control vs contact with first component.

| First Component Treatment | Time (hours) | | | | | |
|---|---|---|---|---|---|---|
| | 0 | 24 | 48 | 72 | 96 | 120 |
| Untreated CL 111 Control | 0% | 0% | 1.3% | 29.3% | 80.0% | 86.7% |
| 3.12 mg/Kg CL 111 seed | 0% | 0% | 2.7% | 42.7% | 92.0% | 94.7% |
| 0.312 mg/Kg CL 111 seed | 0% | 0% | 4.0% | 53.3% | 92.0% | 96.0% |

TABLE 8

Rice Variety CL 151 Germination Rate of control vs contact with first component.

| First Component Treatment | Time (hours) | | | | | |
|---|---|---|---|---|---|---|
| | 0 | 24 | 48 | 72 | 96 | 120 |
| Untreated CL 151 Control | 0% | 1.0% | 32.0% | 65.3% | 73.3% | 76.0% |
| 3.12 mg/Kg CL 151 seed | 0% | 1.5% | 34.7% | 66.7% | 76.0% | 76.0% |
| 0.312 mg/Kg CL 151 seed | 0% | 4.0% | 50.7% | 74.7% | 82.7% | 84.0% |

This experiment demonstrates that the first component as an A.I. applied to hybrid rice as a seed treatment increases both the rate of germination as well as the final percentage of seed that is germinated. Total germination increases were greater than 10% for both varieties with the low rate of A.I. versus the non-treated seed.

Experiment 4

Seedling Mortality Prevention

The purpose of this experiment was to observe the effect of the first component on seedling mortality. While conducting Experiment 3 above, it was observed that for CL 151 seedlings, there was a significant amount of disease in the seedling phase that resulted in high amounts of seedling mortality. As shown in Table 9, both rates of A.I. reduced the incidence of seedling mortality with the lower rate providing the best control.

TABLE 9

Rice Variety CL 151 Seedling Disease Mortality- control vs contact with first component.

| CL 151 Treatment | Mortality % |
|---|---|
| Untreated Control | 25.3 |
| 3.12 mg/Kg seed | 16.0 |
| 0.312 mg/Kg seed | 13.3 |

Experiment 5

Comparative Examples

A seed treatment product (STP) consisting of an NPK fertilizer (11-11-7) with 0.08% Zn, and 0.036% Gibberellic Acid was evaluated for emergence response in soybean seed, and compared with a control and a commercial seed treatment product, ApronMaxx (Syngenta). A fourth treatment sample consisted of a combination of STP and ApronMaxx. Seed was treated with 2 fl. oz. of seed treatment product per 100 pounds of seed and the seed were planted in pots and placed in a greenhouse. There were 6 replicates per treatment. Treatments were evaluated at 4 and 5 days after planting (DAP). Emergence was rated as follows: N-No emergence—0 points; C-Crook, just breaking soil surface—1 point; and E-Fully emerged—2 points. Results are shown in Table 10:

TABLE 10

Emergence data for comparative examples.

| Treatment | Average Rating Time | | | |
|---|---|---|---|---|
| | 5DAP | | 6DAP | |
| Control | 0.356 | b | 0.960 | b |
| STP | 1.306 | a | 1.720 | a |
| ApronMaxx | 0.444 | b | 0.960 | b |
| ApronMaxx + STP | 1.378 | a | 1.710 | a |

Means within columns and borders followed by the same letter Protected LSD are not different at the 5% level of significance (unless noted otherwise) as tested by Fishers Protected LSD.

This experiment demonstrates the effect of STP in speeding up germination and emergence of soybean seeds, compared to the Control and to ApronMaxx. It also shows that when STP was added to ApronMaxx, the emergence was nearly identical to the STP alone and significantly better than the Control or ApronMaxx alone.

Experiment 6

First Component vs Comparative Example and Synergistic Combination of the First component and Comparative Example In an experiment with soybean seed, the first component was compared to STP from Experiment 5 and with a combination of the first component and STP to determine the effect upon rate of germination. This trial was conducted using soybean seed treated with the first component alone, STP alone, or a combination of the first component and STP. In this experiment, 50 seeds were placed on sponges which had been soaked with 500 ml of water (the Control) or with 500 ml water that contained varying amounts of the first component or the first component plus STP. Germination was measured after 48, 72, and 120 hours. Results are shown in Table 11.

TABLE 11

Soybean emergence results with the first component ("CP") and STP.

| Treatment | % Emerged Time | | | |
|---|---|---|---|---|
| | 24 hr | 48 hr | 72 hr | 96 hr |
| Control | 0% | 4% | 18% | 81% |
| 0.6 mg/Kg A.I. + .03% STP | 0% | 3% | 30% | 81% |
| 1.2 mg/Kg A.I. + .03% STP | 0% | 15% | 26% | 92% |
| 0.6 mg/Kg A.I. | 0% | 24% | 44% | 90% |
| 1.2 mg/Kg A.I. | 0% | 24% | 46% | 96% |

This experiment demonstrates that the first component as A.I. alone at either 0.6 mg/Kg or 1.2 mg/Kg rate causes the germination rate to increase faster than the control or the STP plus the first component. 1.2 mg/Kg of first component added to the STP improved performance significantly over the 0.6 mg/Kg of the first component added to the STP. However, when the same experiment was repeated for corn, the results showed the opposite effect. Here, both treatments alone improved germination versus the control, but adding STP to each treatment with the first component resulted in a further enhancement in the germination rates as seen in Table 12.

TABLE 12

Corn emergence results with the first component (A.I.) and STP.

| Treatment | % Emerged Time | | |
|---|---|---|---|
| | 72 hr | 96 hr | 120 hr |
| Control | 0% | 50% | 95% |
| 0.6 mg/Kg A.I. + .03% STP | 10% | 60% | 95% |
| 1.2 mg/Kg A.I. + .03% STP | 15% | 90% | 100% |
| 0.6 mg/Kg A.I. | 5% | 65% | 100% |
| 1.2 mg/Kg A.I. | 10% | 60% | 95% |

In the case of corn, the first component alone improves germination, but there is an additive effect or synergistic effect when the STP is added to the first component as demonstrated by the above experimental data.

Experiment 7

Formulations Comprising the First Component and a Second Component (Pesticide)

The purpose of this experiment was to determine whether the first component, when tank mixed with a non selective herbicide (glyphosate), was able to enhance weed control or the speed of the weed control. The glyphosate formulation used was Roundup Powermax™ from Monsanto. A field trial was established using a Randomized Complete Block (RCB) Design with 3 replicates in each treatment. 4 weed species or weed categories were evaluated: cutleaf evening primrose (*Oenothera laciniate*) OEOLA, narrow-leafed vetch (*Vicia angustifolia*) VICAN, Carolina geranium (*Geranium carolinianum*) GERCA, and other grasses OTGRA. Plots were sprayed with two rates of glyphosate, each with and without the first component, and weed control ratings were made at 7, 14, and 28 days after application (DAA). Weed control was reported as percent of weeds killed out of the original population. Test results are shown in Table 13.

TABLE 13

Weed control of Glyphosate tank mixed first component (A.I.). Means followed by the same letter do not significantly differ (P = 0.10, LSD). Mean comparisons performed only when AOV Treatment P(F) is significant at mean comparison OSL.

| | Rate | Ratings | | | | | | | | | | | |
|---|---|---|---|---|---|---|---|---|---|---|---|---|---|
| | | OEOLA | | | VICAN | | | GERCA | | | OTGRA | | |
| Product(s) | fl oz/ac | 7 DAA | 14 DAA | 28 DAA | 7 DAA | 14 DAA | 28 DAA | 7 DAA | 14 DAA | 28 DAA | 7 DAA | 14 DAA | 28 DAA |
| Roundup Powermax | 22 | 58 a | 55 ab | 76 b | 21 bc | 35 c | 68 b | 21 ab | 40 bc | 51 a | 64 a | 90 b | 99 a |

TABLE 13-continued

Weed control of Glyphosate tank mixed first component (A.I.). Means followed by the same letter do not significantly differ (P = 0.10, LSD). Mean comparisons performed only when AOV Treatment P(F) is significant at mean comparison OSL.

| | | Ratings | | | | | | | | | | | |
|---|---|---|---|---|---|---|---|---|---|---|---|---|---|
| | Rate | OEOLA | | | VICAN | | | GERCA | | | OTGRA | | |
| Product(s) | fl oz/ac | 7 DAA | 14 DAA | 28 DAA | 7 DAA | 14 DAA | 28 DAA | 7 DAA | 14 DAA | 28 DAA | 7 DAA | 14 DAA | 28 DAA |
| Roundup Powermax + A.I. | 22 6 | 60 a | 68 a | 87 a | 25 a | 40 ab | 72 a | 25 a | 45 a | 49 ab | 60 ab | 97 a | 99 a |
| Roundup Powermax | 13.2 | 33 c | 50 b | 59 cd | 17 d | 42 a | 62 d | 17 c | 40 bc | 43 c | 43 cd | 91 c | 99 a |
| Roundup Powermax + A.I. | 13.2 6 | 47 b | 57 ab | 67 c | 23 ab | 42 a | 65 c | 23 ab | 43 ab | 45 c | 47 c | 92 c | 99 a |

This experiment clearly shows that the combination of first component and pesticide (glyphosate) promoted faster response and improved efficacy of broad weed control. The data also demonstrates the ability to use less of the pesticide when combined with the first component with little or no change in pesticide efficiency.

Experiment 8

This experiment was conducted in a manner similar to Experiment 4, except that manganese ($Mn^{+2}$) and zinc ($Zn^{+2}$) micronutrients were combined with the glyphosate and to the combination of the first component and glyphosate. In this case, the purpose was to show that when Mn and Zn are tank mixed with glyphosate and the first component that there is no antagonism between the metals and the glyphosate with regard to the efficacy of weed control. It is generally known that the addition of Zn or Mn to a spray solution of glyphosate will produce a significant loss of efficacy (See, e.g., "Glyphosate interaction with manganese in tank mixtures and its effect on glyphosate absorption and translocation", Bernards et al., Weed Science, 53:787-794. 2005; and Scroggs et al., "Response of Weeds to Zinc-Glyphosate Mixtures", Louisiana Agriculture Magazine, Summer, 2008.). With Zn the loss of weed control efficacy can be 50% or more. In this trial, both the $Zn^{+2}$ and the $Mn^{+2}$ were present as the sulfate salts at concentrations of 6 vol % and 5 vol % respectively. Results are shown in Table 14.

TABLE 14

Weed control of Glyphosate tank mixed with Mn, Zn, and the first component (A.I.). Means followed by the same letter do not significantly differ (P = 0.10, LSD). Mean comparisons performed only when AOV Treatment P(F) is significant at mean comparison OSL.

| | | Ratings | | | | | | | | | | | |
|---|---|---|---|---|---|---|---|---|---|---|---|---|---|
| | Rate | OEOLA | | | VICAN | | | GERCA | | | OTGRA | | |
| Product(s) | fl oz/ac | 7 DAA | 14 DAA | 28 DAA | 7 DAA | 14 DAA | 28 DAA | 7 DAA | 14 DAA | 28 DAA | 7 DAA | 14 DAA | 28 DAA |
| Roundup Powermax | 22 | 58 a | 55 ab | 76 b | 21 b | 35 b | 68 b | 21 ab | 40 bc | 51 ab | 64 a | 90 b | 99 a |
| Roundup Powermax + A.I. | 22 6 | 60 a | 68 a | 87 a | 25 a | 40 a | 72 a | 25 a | 45 a | 49 b | 60 ab | 97 a | 99 a |
| Roundup Powermax + MnSO4 + A.I. | 22 1 qt. ac 6 | 40 bc | 57 ab | 72 bc | 23 ab | 35 b | 67 b | 23 a | 37 c | 61 a | 50 bc | 94 ab | 99 a |
| Roundup Powermax + MnSO4 + ZnSO4 | 22 1 qt. ac 1 qt. ac | 47 b | 65 ab | 78 fg | 23 ab | 37 ab | 65 c | 23 a | 38 c | 43 b | 62 ab | 94 ab | 99 a |

The data of Table 14 demonstrates that in this trial, results for the $Mn^{+2}$ and $Mn^{+2}$ plus $Zn^{+2}$ treatments with the first component were not statistically different than the glyphosate alone, thus showing that there was no substantially antagonism between the glyphosate and these metals when the first component is present.

Experiment 9

An experiment was conducted to determine whether the first component when tank mixed with two non-selective herbicides (glyphosate and glufosinate) was able to enhance weed control or the speed of the control. The glyphosate formulation used was Roundup Powermax™ from Monsanto and the glufosinate was Ignite™ Herbicide from Bayer CropScience. A field trial was established using a Randomized Complete Block (RCB) Design with 3 replicates in each treatment. There were 4 weed species or weed categories evaluated: Canada horseweed (*Erigeron Canadensis*) ERICA, Common dandelion (*Taraxacum officinale*) TAROF, Annual bluegrass (*Poa annua*) POAAN, and Mouse-ear chickweed (*Cerastium vulgatum*) CERVU. Plots were sprayed and each of the herbicides were applied with and without the first component. Weed control ratings were made at 9, 16, and 28 days after application (DAA). Weed control was reported as percent of weeds killed out of the original population. Test results are shown in Table 15.

TABLE 15

Weed control of Glyphosate and Glufosinate tank mixed with the first component (A.I.).
Means followed by the same letter do not significantly differ (P = 0.10, LSD). Mean comparisons performed only when AOV Treatment P(F) is significant at mean comparison OSL.

| | | Ratings | | | | | | | | | | |
|---|---|---|---|---|---|---|---|---|---|---|---|---|
| | Rate | OEOLA | | | VICAN | | | GERCA | | | OTGRA | | |
| Product(s) | fl oz/ac | 7 DAA | 14 DAA | 28 DAA | 7 DAA | 14 DAA | 28 DAA | 7 DAA | 14 DAA | 28 DAA | 7 DAA | 14 DAA | 28 DAA |
| Roundup Powermax | 22 | 38 b | 80 ab | 98 a | 33 d | 55 d | 86 a | 75 c | 97 a | 96 a | 65 b | 99 a | 98 a |
| Roundup Powermax + A.I. | 22 6 | 48 b | 75 abc | 96 ab | 50 c | 62 c | 87 a | 78 bc | 99 a | 95 a | 65 b | 99 a | 98 a |
| Ignite | 23 | 83 a | 75 abc | 92 c | 70 b | 88 b | 96 a | 82 b | 84 c | 58 b | 82 a | 95 b | 95 a |
| Ignite + A.I. | 23 6 | 92 a | 93 a | 94 abc | 85 a | 96 a | 95 a | 90 a | 88 b | 59 b | 92 a | 97 ab | 97 a |

Results in this experiment show the first component significantly enhances the activity for both glyphosate and glufosinate. Thus, the combination of the first component with pesticide is synergistic.

Prophetic Examples

In planta metabolism is generally unpredictable, i.e., one cannot predict from prior traditional uses of a herbicide, what effects may result, especially for genetically modified (GM) plants. For example, dicamba contact of dicamba-tolerant crops (e.g., DMO-expressing crops) would benefit from the compositions and methods disclosed and described herein as the first component likely will regulate one or more genes of the GM dicamba-tolerant crop and as a result, it is generally believed that the compositions and methods would effectively provide one or more of the following:

increase in dicamba metabolites, including DCSA;
increase in dicamba effectiveness or the use of lower levels of dicamba than possible without the first component;
increased resistance of dicamba-tolerant crops against biotic (e.g., insects, fungi, viruses, nematodes, and other pathogens) and abiotic stresses (e.g., drought, cold, ozone, soil nutrient deficiencies), with resulting increases in yields and improved quality of dicamba-tolerant crops;
increase the absorption of multivalent metal ions in dicamba-tolerant crops.

It is further believed that the benefits of the methods and compositions herein disclosed and described would be useful for other GM crops and may further be applicable to the development of such GM crops.

Thus, a method for increasing the germination rate of a seed, is contemplated, comprising contacting the seed with the first component and with dicamba or a product of DMO-mediated metabolism thereof in an amount that improves the germination of the seed as compared to a seed of the same genotype not contacted with the first component and the dicamba or a product of DMO-mediated metabolism thereof. In one aspect, the seed comprises a transgene that encodes DMO All patents and publications cited herein are incorporated by reference into this application in their entirety.

The words "comprise", "comprises", and "comprising" are to be interpreted inclusively rather than exclusively.

What is claimed is:

1. A plant nutrient concentrate composition consisting of, in aqueous solution or dried or lyophilized in a form suitable for reconstitution with an aqueous solution,
   a first component comprising an agriculturally acceptable concentrated complex mixture of dissolved organic material such that the concentration of dissolved organic material is between about 1000 ppm to about 500,000 ppm, the dissolved organic material comprising:
   condensed hydrocarbons, lignins, and tannins and/or condensed tannins;
   an oxygen-to-carbon ratio for the dissolved organic matter of greater than about 0.5;
   a total number of tannin compounds greater than about 200, the tannin compounds having a hydrogen to carbon ratio of about 0.5 to about 1.4, and an aromaticity index of less than about 0.7 as measured by mass spectroscopy; and
   a mass distribution of about 47-56% lignin compounds, 33-42% tannin compounds, and about 8-11% condensed hydrocarbon as measured by mass spectroscopy.

2. The plant nutrient composition of claim 1, wherein the first component is characterized by comprising a mixture of condensed hydrocarbons, lignins, and tannins and/or condensed tannins, characterized in that at least 10% of the total % of compounds of the composition are tannins and/or condensed tannins.

3. The plant nutrient composition of claim 1, wherein the first component is characterized by comprising a mixture of condensed hydrocarbons, lignins, and tannins and/or condensed tannins, characterized in that at least 20% of the total % of compounds of the composition are tannins and/or condensed tannins.

* * * * *